(12) United States Patent
Brockwell

(10) Patent No.: US 6,715,624 B2
(45) Date of Patent: *Apr. 6, 2004

(54) SAMPLE VIAL AND VIAL CLOSURE DEVICE FOR USE IN GAS ANALYSIS AND METHOD OF USING SAME

(75) Inventor: Timothy Graham Brockwell, Sandbach (GB)

(73) Assignee: Micromass UK Limited, Manchester (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/967,410

(22) Filed: Nov. 11, 1997

(65) Prior Publication Data

US 2002/0066712 A1 Jun. 6, 2002

(30) Foreign Application Priority Data

Nov. 12, 1996 (GB) .............................. 96235445

(51) Int. Cl.⁷ .............................................. B65D 41/20
(52) U.S. Cl. .................... 215/247; 215/274; 215/276; 215/308; 215/311; 215/315; 215/355; 604/249; 73/863.85; 73/863.86
(58) Field of Search ...................... 222/402.25, 509, 222/518, 80, 501; 215/247, 355, 273, 274, 276, 280, 281, 283, 310, 311, 308, 315; 73/863.85, 863.86; 604/33, 249

(56) References Cited

U.S. PATENT DOCUMENTS

| | | | |
|---|---|---|---|
| 2,529,964 A | * 11/1950 | Raab ...................... 215/311 X |
| 2,557,917 A | * 6/1951 | Schlesinger ............. 222/501 X |
| 2,844,964 A | * 7/1958 | Guibert ................... 73/863.86 |
| 3,091,374 A | * 5/1963 | Schwartzman .......... 222/518 X |
| 3,106,321 A | * 10/1963 | Gorman ..................... 22/509 X |
| 3,238,784 A | * 3/1966 | Dorsey et al. ........... 73/863.85 |
| 3,353,411 A | 11/1967 | Nadeau et al. |
| 3,603,471 A | 9/1971 | Harris et al. |
| 3,754,434 A | 8/1973 | Guild |
| 3,754,443 A | 8/1973 | Harris, Sr. et al. |

(List continued on next page.)

FOREIGN PATENT DOCUMENTS

| | | | |
|---|---|---|---|
| CA | 984211 | * 3/1975 | ................. 215/247 |
| DE | 2824588 | * 12/1975 | ................. 215/247 |
| IT | 484928 | * 9/1953 | ................. 215/247 |
| RU | 1673952 A1 | 8/1991 | |

Primary Examiner—Robin A. Hylton
(74) Attorney, Agent, or Firm—Alix, Yale & Ristas, LLP

(57) ABSTRACT

A vial closure device, a sample vial incorporating such a vial closure device, and certain methods of using such a vial and closure device. The vial and closure device are intended to contain a gaseous sample or a headspace gas present above a liquid or solid material, so that the gaseous sample or headspace gas can be conveniently analysed, typically by means of an autosampler connected to an analytical instrument such as a mass spectrometer. Mass spectrometric methods of determining the isotopic composition of hydrogen and oxygen comprised in aqueous samples contained in vials fitted with such closure devices are disclosed. The vial closure device comprises a hollow body member locatable in the mouth of a vial, and a first seal for making a substantially gas-tight seal between the exterior of said hollow body member and said vial. The hollow body member comprises an aperture and an aperture closing means for closing said aperture when required, and a second seal, through which a gas sampling means may be inserted. The aperture closing means is operable to open the aperture by the insertion of a gas sampling means through the second seal and is operable to close the aperture when the gas sampling means is withdrawn.

3 Claims, 3 Drawing Sheets

U.S. PATENT DOCUMENTS

| | | | |
|---|---|---|---|
| 3,757,981 A | | 9/1973 | Harris, Sr. et al. |
| 3,885,438 A | | 5/1975 | Harris, Sr. et al. |
| 3,930,413 A | * | 1/1976 | Laird et al. .............. 73/863.85 |
| 3,940,995 A | | 3/1976 | Harris, Sr. et al. |
| 4,000,654 A | | 1/1977 | Harris, Jr. |
| 4,044,616 A | | 8/1977 | Harris, Sr. et al. |
| 4,056,981 A | * | 11/1977 | Kalka et al. .............. 73/863.85 |
| 4,084,718 A | * | 4/1978 | Wadsworth ................. 215/247 |
| 4,094,197 A | | 6/1978 | Harris, Sr. et al. |
| 4,121,465 A | | 10/1978 | Harris, Sr. et al. |
| 4,134,512 A | | 1/1979 | Nugent |
| 4,478,095 A | | 10/1984 | Bradley et al. |
| 4,600,221 A | * | 7/1986 | Bimba ........................ 285/91 |
| 4,704,141 A | | 11/1987 | Krebber |
| 4,854,181 A | | 8/1989 | Gerstel |
| 4,887,472 A | * | 12/1989 | Jansen ..................... 73/863.86 |
| 4,932,543 A | * | 6/1990 | Martus ................... 215/247 X |
| 4,960,218 A | * | 10/1990 | Toida et al. ................ 215/311 |
| 5,012,845 A | | 5/1991 | Averette |
| 5,032,151 A | | 7/1991 | Klein et al. |
| 5,046,645 A | * | 9/1991 | Hagan et al. ........... 222/518 X |
| 5,062,310 A | | 11/1991 | Eaton |
| 5,088,612 A | * | 2/1992 | Storar et al. ................ 215/247 |
| 5,146,792 A | * | 9/1992 | Iff ........................... 73/863.86 |
| 5,242,393 A | * | 9/1993 | Brimhall et al. ........ 604/249 X |
| 5,297,431 A | | 3/1994 | White |
| 5,431,067 A | * | 7/1995 | Anderson et al. ........ 73/863.86 |
| 5,432,098 A | | 7/1995 | Wilks |
| 5,441,700 A | | 8/1995 | Markelov |
| 5,456,126 A | | 10/1995 | Suddath |
| 5,458,640 A | * | 10/1995 | Gerrone .................. 604/249 X |
| 5,578,059 A | * | 11/1996 | Patzer ........................ 604/249 |
| 5,584,808 A | * | 12/1996 | Healy ..................... 604/249 X |
| 5,584,850 A | * | 12/1996 | Hart et al. |
| 5,586,673 A | * | 12/1996 | Venooker et al. ....... 215/276 X |
| 5,620,434 A | * | 4/1997 | Brony .................... 604/249 X |
| 5,735,826 A | * | 4/1998 | Richmond .............. 604/249 X |
| 5,880,380 A | * | 3/1999 | Goldschmidt et al. ... 73/863.85 |
| 5,932,482 A | * | 8/1999 | Markelov ................... 422/102 |
| 5,945,070 A | * | 8/1999 | Kath et al. |
| 6,255,101 B1 | * | 7/2001 | Rousseau et al. ........... 215/247 |

* cited by examiner

SAMPLE VIAL AND VIAL CLOSURE DEVICE FOR USE IN GAS ANALYSIS AND METHOD OF USING SAME

FIELD OF THE INVENTION

This invention relates to a closure device for a sample vial, and a sample vial incorporating such a device, for containing a gaseous sample or a headspace gas which is to be analysed present above a liquid or solid sample. In particular it relates to a vial and vial closure device especially suitable for containing aqueous samples and methods of determining the isotopic composition of oxygen or hydrogen comprised in aqueous samples contained in such vials by mass spectrometry.

BACKGROUND OF THE INVENTION

Conventional sample vials for automatic samplers typically comprise a small glass vessel which may be closed by a rubber septum held in place by a cap attached to the vessel by a screw thread or by crimping. After sealing, a number of such vials may be loaded into an autosampler which extracts a sample from each vial in turn and sends it for analysis by any desired analytical instrument, for example a chromatograph or spectrometer. Both gaseous and liquid samples may be analysed in this way. In some cases, the vial may be partially filled with a liquid sample but only gas present in the space above the liquid (the headspace gas) may be sampled. Typically, the autosampler will comprise a syringe whose needle, under computer control, is caused to pierce the septum of a selected vial so that a sample of gas or liquid can be withdrawn through the needle and analysed. The septum maintains a gas-tight seal around the needle during this process to prevent contamination. Means are provided to align a second vial with the syringe after the first one has been sampled so that many vials may be sampled automatically in sequence. Means may also be provided for cleaning the syringe between samples.

For the majority of samples, silicone rubber septa may be used to close the vial, but where there is a possibility of reaction of the vial contents with a conventional septum, a septum lined with an inert material, such as PTFE or Teflon, may be employed. These are used with the PTFE lining in contact with the vial contents so that the contents are protected from contact with the rubber septum while the rubber portion still provides a good seal around the needle. A septum made from a solid material such as PTFE is generally incapable of providing an adequate seal around the needle. Unfortunately, lined septa of this type have a limited lifetime because the lining is usually damaged by insertion of the needle, leaving an area of silicone rubber in contact with the vial contents.

This problem has been addressed by the provision of sample vial closure devices which incorporate a shut-off valve as well as a septum. When the valve is opened, a syringe needle may be passed through it to allow the vial contents to be sampled. A silicone rubber septum or seal, through which the needle must also pass, is also provided to seal the vial while the needle is inserted because the valve itself is unable to seal to the needle. Vial closure devices of this type are disclosed in U.S. Pat. Nos. 3,757,981 and 3,603,471, and are commercially available (for example, "Mininert" valves available from Sigma-Aldrich Company Ltd.).

The vial closure device taught in U.S. Pat. No. 3,603,471 comprises a first tube fitted to the screw cap of a conventional glass vial, through which tube a syringe needle may be inserted. A valve stem comprising a second tube is disposed in a bore perpendicular to the axis of the first tube and may be rotated therein by means of an external handle. The second tube comprises a hole perpendicular to its axis which may be aligned with the bore of the first tube by rotation by the handle to open the valve and allow unobstructed passage of a syringe needle through the first tube into the vial. A plug type rubber septum is inserted into the bore of the second tube so that it is pierced by the syringe needle as it is inserted through the device when the valve is open. In this way the contents of the vial are exposed to the septum only for the short time that the valve is open, minimising contamination. U.S. Pat. No. 3,757,981 teaches a variation on this design in which the second tube is replaced by a rod having a bore perpendicular to its axis which may be aligned with the bore of the first tube by sliding the rod. In this device, the septum is placed in the entrance of the first tube. The currently available "Mininert" valves are of this general design.

In some analyses it is necessary to sample only the headspace gas from a vial. One example of this is the measurement of the isotopic composition of hydrogen and/or oxygen in samples of water. In this method a sample of water is placed in a vial which is then sealed. A quantity of carbon dioxide (for oxygen analysis) or hydrogen (for hydrogen analysis) of accurately known isotopic composition is then injected into the vial and allowed to equilibrate with the water. After a suitable time has elapsed, a sample of the headspace gas is withdrawn and its isotopic composition is determined by mass spectrometric analysis. The original isotopic composition of the hydrogen or oxygen present in the water can then be determined from the change in the isotopic composition of the headspace gas during equilibration. Unfortunately, prior attempts to automate this process have not been successful because of losses or contamination of the headspace gas arising from contact with the rubber septum (or a lined septum after it has been punctured to admit the equilibration gas) during the equilibration process. Prior types of valved vials have also proved unsatisfactory, firstly because they cannot easily be used with conventional autosamplers, requiring manual operation of the valve handle, and secondly because the surface area of the material from which the devices are made (PTFE) is so large that contamination or loss of the headspace gas can still occur.

SUMMARY OF THE INVENTION

It is an object of the invention to provide an improved vial closure device incorporating a valve which is suitable for closing a vial from which a gaseous sample is required, and which is suitable for use with conventional autosamplers. It is another object of the invention to provide a vial comprising such a closure device. It is another object of the invention to provide a method of using such a vial for the determination of the isotopic composition of a sample contained in it, and apparatus for carrying out that method.

The invention therefore provides a vial closure device for closing the mouth of a vial which may contain a gas or vapor to be analyzed by extraction through a gas sampling means connected to an analytical instrument, said vial closure device comprising:— a) a hollow body member locatable in the mouth of a said vial; and
b) first sealing means for making a substantially gas-tight seal between the exterior of said hollow body member and a said vial;

said hollow body member further comprising:—
a) an aperture through which gas present in a said vial may pass into the interior of said hollow body member;
b) aperture closing means for closing said aperture when required; and
c) second sealing means, through which a said gas sampling means may be inserted into said interior, for allowing a said gas sampling means to enter said interior while maintaining a seal around it;

characterised in that said aperture closing means is operable to open said aperture by the insertion of a gas sampling means through said second sealing means and is operable to close said aperture when said gas sampling means is withdrawn.

In preferred embodiments, the aperture comprises a valve seat and the aperture closing means comprises a valve body which is maintained in engagement with the valve seat, thereby closing the aperture, by the action of a spring. The valve seat and body may be disposed so that when a gas sampling means is inserted sufficiently far into the interior of said hollow body member it contacts and displaces a valve spindle, which action displaces the valve body from the valve seat and opens the aperture. On withdrawal of the gas sampling means, the spring restores the valve spindle and body to their former positions and closes the aperture. Preferably the valve body and seat are further disposed so that it is also possible to insert a gas sampling means far enough through the second sealing means to allow gas to be withdrawn from the interior of the hollow body member but not far enough to displace the valve spindle. Typically, a gas sampling means suitable for use with the invention will comprise a hollow syringe needle closed at one end which may be inserted into the interior of the hollow body member through the second sealing means and which has a side aperture adjacent to the closed end through which gas may pass into the needle.

It will be appreciated that valuable features of the invention are that the gas sampling means can contact the aperture closing means to open it and that the gas sampling means need not pass through the aperture.

In one preferred embodiment the second sealing means may operate to close the interior of the hollow body member in the absence of a gas sampling means. For example, the hollow body member may comprise a tube, closed at one end with a plate having the aperture and at the other end with the second sealing means which may comprise a conventional rubber septum secured by a screw cap which engages with a thread on the exterior of the hollow body member. In this way the interior of the hollow body member may be made substantially gas-tight. In operation, a syringe needle of the type described above may be inserted through the septum into the interior of the hollow body member, allowing gas to be withdrawn from it, and if further inserted will contact the valve spindle, displacing the valve body to open the aperture so that gas may be introduced into or withdrawn from the vial as well as the interior of the hollow body member.

In other preferred embodiments, however, the second sealing means may seal only to a gas sampling means inserted into the hollow body member, and may not close the interior of the hollow body member when the sampling means is not present. Typically, the second sealing means may then comprise one or more "O" rings located in grooves on the interior of the hollow body member which seal to a gas sampling means when it is inserted, to make the interior of the hollow body member substantially gas-tight.

In other preferred embodiments the exterior portion of the hollow body member is provided with a flange which overlaps the top of a sample vial when the hollow body member is located in the mouth of that vial. In such a case the first sealing means may comprise a rubber or plastic washer disposed between the top of the vial and the flange, and the hollow body member may be secured to the vial by a threaded retaining ring passed over the hollow body member and engaged with threads on the exterior of the vial, so that on tightening the retaining ring the flange is pressed down on the washer against the top of the vial to provide a gas-tight seal.

Alternatively, the first sealing means may comprise a standard tapered joint, optionally fitted with an "O" ring. Typically, the exterior of the hollow body member may be formed into a taper to engage a suitable tapered socket on the sample vial. Such an arrangement permits the use of a closure device according to the invention with any vial having a suitable tapered joint. Further preferably, in order to prevent the joint separating in the event of the pressure inside the vial exceeding atmospheric pressure, the vial may be provided with an external lip at the entrance to the tapered joint under which a third sealing means, for example an 'O' ring, may be located. The hollow body member may then be secured to the vial by means of a flanged retaining ring which engages with the hollow body member. The retaining ring is preferably such that it will pass over the lip (and/or the vial body) in the absence of the third sealing means but is capable of securing the third sealing means between its flange and the lip. The retaining ring may conveniently engage the exterior of the hollow body member by a screw thread.

Viewed from another aspect the invention provides a sample vessel which may contain a gas or vapor to be analyzed by extraction through a gas sampling means connected to an analytical instrument, said sample vessel comprising a vial fitted with a vial closure device as defined above.

Preferably the hollow body member and the valve seat of the invention are made from stainless steel and the valve body is made from polychlorotrifluoroethylene or a similar inert polymeric material. The vials may be conventional glass or quartz vials.

The chief advantage of a vessel and vial closure device according to the invention is that the contents of the vial are exposed only to a minimal area of rubber or polymeric material, that is, only a part of the valve body which can be made very small. This is in contrast with prior valved vials in which the whole of the closure device is typically made from PTFE, presenting a large surface area to the vial contents. Also, the valve itself is operated automatically by insertion of a gas sampling means (needle), permitting their use with a suitably programmed conventional autosampler.

Use of a vial and closure device according to the invention facilitates the automatic isotopic analysis of hydrogen and oxygen comprised in aqueous or other liquid samples. This may be done by equilibrating the sample in a vial with a sample of an equilibration gas (carbon dioxide for oxygen isotope determination or hydrogen for hydrogen isotope determination) of accurately known isotopic composition, and subsequently withdrawing a sample of the headspace gas and determining the new isotopic composition of the carbon dioxide or hydrogen using an isotopic ratio mass spectrometer. Viewed from another aspect, therefore, the invention comprises a method of using a vial closure device as defined above for the isotopic analysis of a liquid sample contained in a vial closed by a device as defined above, said method comprising the steps of:—
a) inserting a gas sampling means into the interior of said hollow body member through said second sealing means;

b) removing residual gas in said vial and the interior of said hollow body member;

c) introducing through said gas sampling means into said vial an equilibration gas of known isotopic composition;

d) removing said gas sampling means from said interior of said hollow body member and allowing the sample contained in said vial to equilibrate with said equilibration gas;

e) inserting a gas sampling means into the interior of said hollow body member through said second sealing means;

f) removing residual gas from the interior of said hollow body member through said gas sampling means;

g) sampling headspace gas from the interior of said vial through said gas sampling means;

h) conveying a said sample of headspace gas to an isotopic ratio mass spectrometer and determining its isotopic composition;

i) calculating the isotopic composition of an element comprised in said sample from the change in the isotopic composition of said equilibration gas caused by the equilibration of said equilibration gas with said sample.

In this method, the steps of removing residual gas may comprise either evacuating the gas through the gas sampling means or purging the space occupied by the gas to be removed with a gas which does not contain the element to be analysed. In the latter case, the gas sampling means may comprise a twin-needle device so that gas can be introduced though one needle and extracted through the other. Preferably the needles are coaxially disposed.

In preferred embodiments of the method, the gas sampling means is inserted according to step a) so that gas may be removed from the interior of the hollow body member but the aperture closing means is not actuated by the insertion means. When this is done by evacuation, the pressure in the hollow body member may be monitored to ensure that a leak-tight seal has been made between the gas sampling means and the second sealing means. When this has been established, the gas sampling means may be further inserted so that the aperture between the vial and the interior of the hollow body member is opened, and residual gas removed in accordance with step b), again monitoring the pressure to ensure that the vial does not leak. Similarly, in steps e) and f), the gas sampling means is inserted only as far as necessary to allow gas to be removed from the interior of the hollow body member, after which it is further inserted to open the aperture and allow gas from the interior of the vial to be sampled in accordance with step g).

In a further preferred embodiment, after the equilibration gas has been introduced in the above method, the gas sampling means may initially be withdrawn sufficiently to operate the aperture closing means to close the aperture but so that it remains in communication with the interior of the hollow body member. Any residual gas may then be removed before the gas sampling means is completely withdrawn from the second sealing means. Inclusion of this step minimises the risk of a slight leak across the aperture closing means contaminating the headspace gas during the equilibration step.

It will be appreciated that the method of the invention may be automated so that the gas sampling means may comprise the syringe needle of an autosampler connected by suitable automatically controlled valves to a vacuum pump to remove residual gas and to an isotopic ratio mass spectrometer. The autosampler may be programmed to insert the needle into the vials in the manner described above. In this way many different samples, each contained in vials fitted with a closure device according to the invention, can be analysed without operator intervention. Defective vials may be automatically rejected by monitoring the pressure during the gas removal steps of the method without disrupting the analysis of the remaining samples.

Also, in the event that the second sealing means is found to be defective when the interior of the hollow body member is evacuated with the aperture closing means closing the aperture, the vial comprising the defective sealing means may be rejected for analysis at that time, but a replacement second sealing means can be fitted to the vial and the sample subsequently analysed without affecting the integrity of the sample it contains.

The gas sampling means used in steps a) and e) may conveniently comprise the same apparatus, but different assemblies may be used if desired.

Viewed from another aspect the invention provides apparatus comprising a plurality of sample vials for containing a gaseous sample to be analyzed and fitted with a vial closure device, autosampler means comprising a gas sampling means, and means for aligning each of said sample vials with said gas sampling means to allow a said gaseous sample to be taken from each vial in turn by the insertion of said gas sampling means through said vial closure device into said vial, and means for conveying to an analytical instrument at least some of said sample of gaseous sample so taken; said apparatus being characterised in that each said vial closure device comprises:

a) a hollow body member located in the mouth of a said vial; and b) first sealing means making a substantially gas-tight seal between the exterior of said hollow body member and said vial;

said hollow body member further comprising:— a) an aperture through which gas present in a said vial may pass into the interior of said hollow body member;

b) aperture closing means for closing said aperture when required; and c) second sealing means, through which a said gas sampling means may be inserted into said interior, for allowing a said gas sampling means to enter said interior while maintaining a seal around it;

wherein said aperture closing means is operable to open said aperture by the insertion of a gas sampling means through said second sealing means and is operable to close said aperture when said gas sampling means is withdrawn.

BRIEF DESCRIPTION OF THE DRAWINGS

Preferred embodiments of the invention will now be described in detail by way of example only and with reference to the figures, in which.

DESCRIPTION OF PREFERRED EMBODIMENTS

Figure 1:
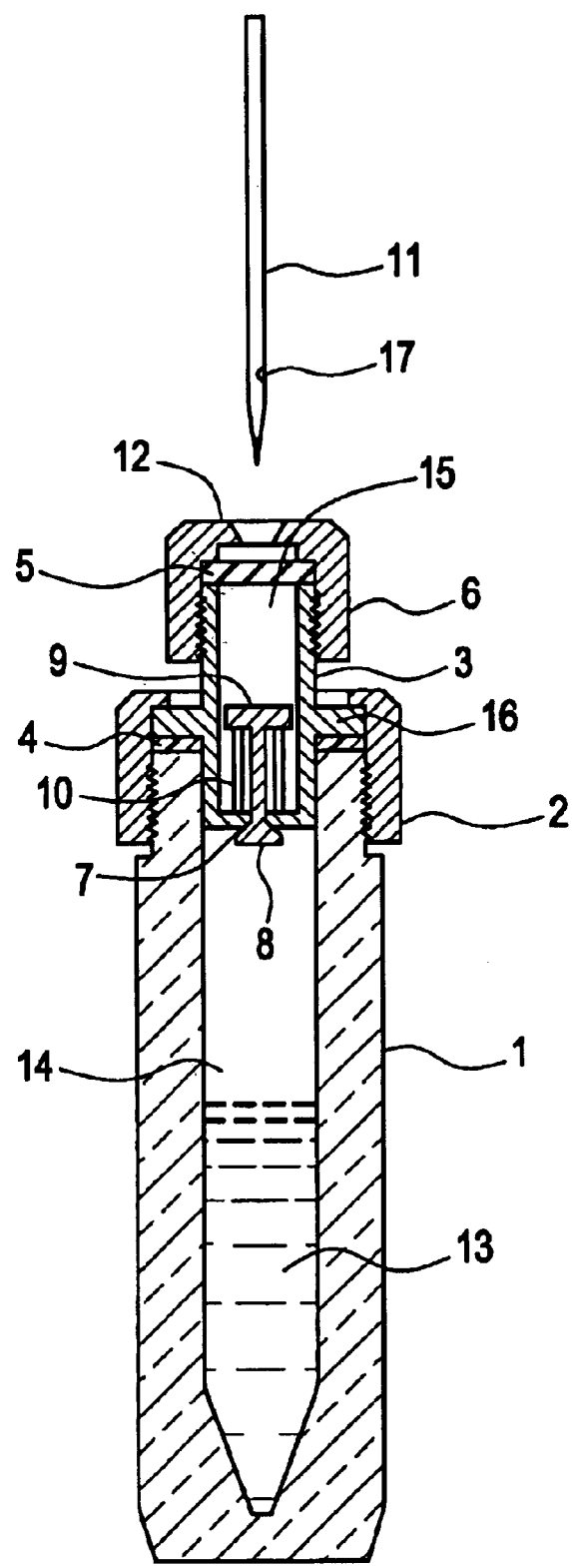
FIG. 1 is a sectional view of one type of a vial closure device according to the invention fitted to a conventional vial.

Referring first to FIG. 1, a conventional glass vial 1 has a screw cap or retaining ring 2 which engages with a thread on the exterior of the vial. A hollow body member 3, conveniently made from stainless steel, has a flange 16 on its exterior and is located in the mouth of the vial 1 as shown.

First sealing means comprising a rubber or PTFE washer 4 is disposed between the flange 16 and the top of the vial 1, and seals the exterior of the hollow body member 3 to the vial 1 by the pressure exerted on it by the screw cap 2 when it is tightened on the vial.

Second sealing means 5 comprise a silicone rubber septum which is disposed at the top of the hollow body member 3 as shown. It is secured by means of a screw cap 6 which engages with a thread cut on the exterior of the hollow body member 3. The cap 6 comprises a hole 12 through which a gas sampling means 11 (comprising a hollow syringe needle) may be introduced into the interior 15 of the hollow body member 3 by piercing the second sealing means 5. As in the case of a septum fitted to a conventional vial, the sealing means 6 makes a substantially gas-tight seal with the gas sampling means 11 when the latter is inserted into the interior 15 of the hollow body member 3. The hollow needle comprising the gas sampling means 11 is sharply pointed but sealed at the tip, and has an aperture 17 formed in its wall to allow gas to enter the needle. This arrangement is preferred over a conventional needle having an opening at the tip because if such a needle were used its tip may suffer damage resulting in closure of that opening through contact with the aperture closing means, as discussed below.

The lower portion of the hollow body member 3 is closed by a plate comprising an aperture communicating between the interiors of the hollow body member 3 and the vial 1. The aperture comprises a countersunk hole which serves as a valve seat 7. Aperture closing means comprise a valve body 8 which is shaped to make a gas-tight seal with the valve seat 7, and a spindle 9 to the lower end of which the body 8 is secured. A spring 10 maintains the valve body 8 in sealing contact with the valve seat 7. The valve body 8 is made from polychlorotrifluoroethylene.

In operation, communication between the interior of the hollow body member 3 and the vial 1 is established by inserting the gas sampling means 11 sufficiently far through the second sealing means 5 that its tip depresses the top of the valve spindle 9, displacing the valve body 8 from the valve seat 7 and allowing gas to pass from the vial to the interior of the hollow body member 3 or vice versa. On withdrawing the gas sampling means 11 the spring 10 restores the valve body to its rest position, closing the aperture and preventing gas flow.

Figure 2:
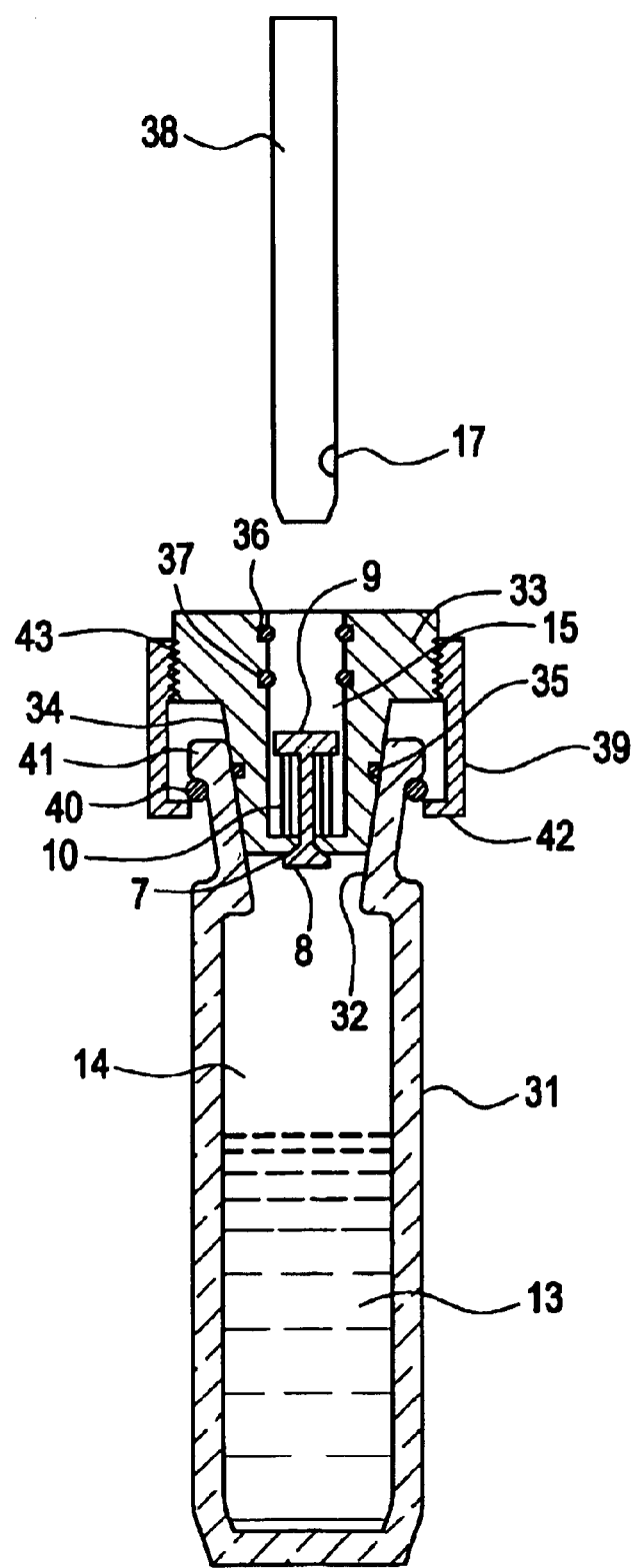
FIG. 2 is a sectional view of another type of vial closure device according to the invention fitted to a different type of vial.

Referring next to FIG. 2, a glass vial 31 has a conventional ground glass tapered joint socket 32. A hollow body member 33 has an exterior surface 34 which is formed to mate with the joint socket 32. An "O" ring 35 is also provided in the joint. Items 32–35 comprise first sealing means as defined above in general terms. Second sealing means comprise a pair of "O" rings 36, 37 fitted in grooves in the interior of the hollow body member 33 as shown. These "O" rings make a substantially gas tight seal with a gas sampling means 38 when it is inserted into the hollow body member 33. In order to ensure that the tapered joint is not separated in the event of the pressure in the vial being greater than atmospheric pressure, a flanged retaining ring 39 is provided to secure a third sealing means 40 (another "O" ring) between an external lip 41 on the vial and a flange 42 on the retaining ring 39. The flanged retaining ring is threaded to engage with a thread 43 cut on the exterior of the hollow body member 33. A valve mechanism comprising items 7,8,9, and 10 is provided and operates as the similar valve arrangement shown in FIG. 1.

Figure 3:
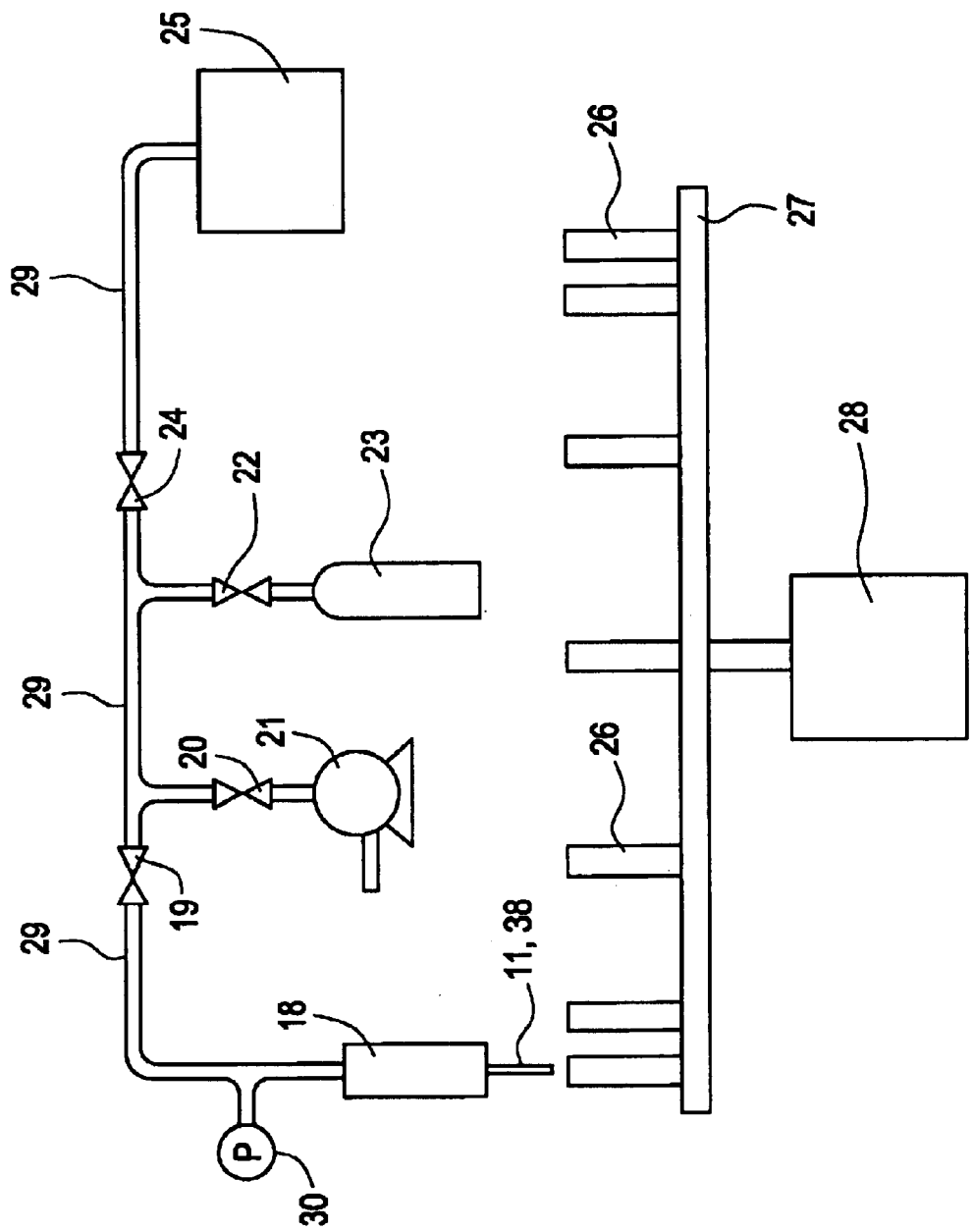
FIG. 3 is a schematic drawing showing apparatus suitable for carrying out methods of the invention.

Referring next to FIG. 3, apparatus for carrying out methods of the invention comprises a turntable 27 driven by a stepping motor 28. A plurality of sample vials 26, each having closures substantially as described and containing a gas to be analysed are located in recesses in the turntable 27 so that as it is rotated by the motor 28 each vial is aligned in turn with a gas sampling means 11 comprising a syringe needle. Also provided is a syringe actuator 18, capable of lowering the syringe needle comprised in the gas sampling means 11 (FIG. 1) or 38 (FIG. 2) so that it enters the second sealing means 5 (FIG. 1) or 36 (FIG. 2) of any vial aligned with it to place the side aperture 17 in communication with the gas in the interior 15 of the hollow body member 3 (FIG. 1) or 33 (FIG. 2), four vacuum isolating valves 19, 20, 22 and 24, a vacuum pump 21, a reservoir of equilibration gas 23, and an analytical instrument 25, in this case an isotopic ratio mass spectrometer, interconnected by narrow bore stainless steel pipe 29 as shown in FIG. 3. A pressure gauge 30 may also be advantageously provided.

In order to sample gas from any one of the vials 26, the motor 28 is caused to rotate until the desired one of the vials 26 is aligned with the gas sampling means 11 or 38. The syringe actuator 18 then lowers the gas sampling means 11 or 38 so that the syringe needle enters the second sealing means 5 or 36, but stops short of contact with the valve spindle 9, while a seal is maintained around the gas sampling means 11 or 38. Gas contained in the interior 15 of the hollow body member 3 or 33 of the vial is then removed by the pump 21 by opening the isolation valves 19 and 20 (while valves 22 and 24 remain closed). In order to establish that the seal and closure means are leaktight, and consequently avoid an inaccurate analysis, valve 19 may then be closed and the pressure in the interior 15 of the hollow body member 3 or 33 monitored for a suitable period. If the pressure rises significantly during this period, the vial or closure means is presumably defective and the analysis may be abandoned. To proceed with the analysis, valve 20 is closed and the syringe actuator 18 caused to lower the gas sampling means 11 or 38 further into the vial so that the syringe needle contacts the valve spindle 9 and opens the aperture between the vial interior and the interior 15 of the hollow body member 3 or 33. Valves 19 and 24 are then opened so that gas from the interior of the vial may enter the analytical instrument 25 When the analysis is complete, valves 19 and 24 are closed and the syringe actuator 18 is caused to withdraw the needle from the vial. This action causes the valve spindle 9 to be restored to its original position by the action of the spring 10, isolating the vial contents from the interior 15 of the hollow body member 3 or 33. The motor 28 may then rotate the turntable to align the next vial to be analysed into alignment with the gas sampling means 11 or 38 and the process may be repeated. Control of the motor 28, the syringe actuator 18 and the valves 19, 20 and 24 is by means of a suitably programmed computer (not shown).

In order to carry out the determination of the isotopic composition of hydrogen or oxygen comprised in aqueous samples, each vial is partially filled with the aqueous sample to be analysed and the vials closed with closure devices substantially as described and placed on the turntable 27. A reservoir 23 is filled with an equilibration gas of accurately known isotopic composition (carbon dioxide in the case of oxygen determination, hydrogen in the case of hydrogen determination). The analytical instrument 25 is an isotopic ratio mass spectrometer adjusted to simultaneously monitor the mass-to-charge ratios appropriate to hydrogen or carbon dioxide analysis. To carry out the analysis, one of the vials to be analysed is aligned with the gas sampling means 11 or 38 and the needle lowered by the syringe actuator 18 to enter the second sealing means 5 or 36 as described above. The interior 15 of the hollow body member 3 or 33 is then evacuated, checked for leaks as described above, and the valve spindle 9 depressed by lowering the needle further, also as described above. The headspace above the aqueous sample in the vial is then evacuated through valves 19 and 20, after which valve 20 is closed and a quantity of equilibration gas from the reservoir 23 is admitted into the vial through valves 22 and 19 with valves 20 and 24 closed. When several vials are to be analyzed, the needle may then be withdrawn from the vial and the next vial to be analyzed may be aligned with the gas sampling means 11 or 38 and filled with equilibration gas in the same manner. In this way the vials may be filled with equilibration gas while time is allowed for previously filled vials to undergo equilibration. After the desired equilibration time the first vial is realigned with the gas sampling means 11 and the headspace gas sampled and conveyed to the mass spectrometer in the manner described above. The resulting measurement of the isotopic composition of the equilibration gas after it has undergone equilibration with the aqueous sample in the vial may then be used to calculate the isotopic composition of the aqueous sample in the vial, using the knowledge of its original isotopic composition, according to conventional practice. After headspace gas has been sampled from the first vial filled with equilibration gas, the second vial so filled is aligned with the gas sampling means and the gas contained in it sampled in the same way.

In this way a vial and vial closure device according to the invention can be used to automate analyses which previously required time consuming manual operation. The above method and apparatus for isotopic analysis is possible only with vials and closure devices of the type described as prior types of valved vials are unsuitable for this process, as explained. However, it will be understood that the vials and closure devices can be used for the automatic analysis of a gaseous sample by use with an appropriate analyser and suitably programmed autosampler. Even if the analyser requires a gas sample at atmospheric pressure, this may be provided simply by initially pressurising the vial with a suitable gas after the closure device has been fitted, or by use of a gas-tight syringe as part of the gas sampling means 11 or 38. In the latter case, gas may be sampled from the vial by withdrawing the syringe plunger once the needle has been inserted into the vial, after which the syringe is completely withdrawn by the syringe actuator 18. The syringe is then suitably repositioned and then operated to inject the gas it contains into the analytical instrument 25. Such a method of operation is provided by many conventional autosamplers.

What is claimed is:

1. A vial closure device for closing the mouth of a vial which in use contains one of a gas and vapor to be analyzed by extraction through a gas sampling device which is connected to an analytical instrument and is displaceable along a sampling axis, said vial closure device comprising:
    a tubular body member having opposite ends and locatable in the mouth of the vial, said tubular body member having at one end an aperture through which gas may pass from the vial into said tubular body member, said tubular body member further comprising a valve seat;
    a first seal for making a substantially gas-tight seal between said tubular body member and the vial;
    a second seal arranged on said sampling axis at the other end of said tubular body member for providing a gas-tight seal around the gas sampling device inserted through said second seal into said tubular body member;
    a valve body which cooperates with said valve seat, said aperture being closed by said valve body to prevent gas from passing from the vial into said tubular body member until said valve body is displaced along a valve axis by contact with the gas sampling device inserted into said tubular body member through said second seal by displacement along said sampling axis, thereby allowing gas to pass from the vial into said tubular body member and the gas sampling device; wherein
    a) said valve axis and said sampling axis are disposed so that said valve body always prevents the gas sampling device from being inserted beyond said valve body into the vial;
    b) said valve seat and said valve body are arranged so that the gas sampling device may be inserted far enough through said second seal so as to allow gas to be withdrawn from the interior of said tubular body member without displacing said valve body; and
    c) the gas sampling device makes a gas-tight seal to the second seal before the valve body is displaced; and wherein said second seal operates to close the interior of said tubular body member in the absence of the gas sampling device to make the interior of said tubular body member substantially gas-tight.

2. A vial closure device for closing the mouth of a vial which in use contains one of a gas and vapor to be analyzed by extraction through a gas sampling device which is connected to an analytical instrument and is displaceable along a sampling axis, said vial closure device comprising:
    a tubular body member having opposite ends and locatable in the mouth of the vial, said tubular body member having at one end an aperture through which gas may pass from the vial into said tubular body member, said tubular body member further comprising a valve seat;
    a first seal for making a substantially gas-tight seal between said tubular body member and the vial;
    a second seal arranged on said sampling axis at the other end of said tubular body member for providing a gas-tight seal around the gas sampling device inserted through said second seal into said tubular body member;
    a valve body which cooperates with said valve seat, said aperture being closed by said valve body to prevent gas from passing from the vial into said tubular body member until said valve body is displaced along a valve axis by contact with the gas sampling device inserted into said tubular body member through said second seal by displacement along said sampling axis, thereby allowing gas to pass from the vial into said tubular body member and the gas sampling device; wherein
    a) said valve axis and said sampling axis are disposed so that said valve body always prevents the gas sampling device from being inserted beyond said valve body into the vial;
    b) said valve seat and said valve body are arranged so that the gas sampling device may be inserted far enough through said second seal so as to allow gas to be withdrawn from the interior of said tubular body member without displacing said valve body; and
    c) the gas sampling device makes a gas-tight seal to the second seal before the valve body is displaced; and wherein said second seal comprises a septum.

3. A vial closure device for closing the mouth of a vial which in use contains one of a gas and vapor to be analyzed by extraction through a gas sampling device which is connected to an analytical instrument and is displaceable along a sampling axis, said vial closure device comprising:

a tubular body member having opposite ends and locatable in the mouth of the vial, said tubular body member having at one end an aperture through which gas may pass from the vial into said tubular body member, said tubular body member further comprising a valve seat;

a first seal for making a substantially gas-tight seal between said tubular body member and the vial;

a second seal arranged on said sampling axis at the other end of said tubular body member for providing a gas-tight seal around the gas sampling device inserted through said second seal into said tubular body member;

a valve body which cooperates with said valve seat, said aperture being closed by said valve body to prevent gas from passing from the vial into said tubular body member until said valve body is displaced along a valve axis by contact with the gas sampling device inserted into said tubular body member through said second seal by displacement along said sampling axis, thereby allowing gas to pass from the vial into said tubular body member and the gas sampling device; wherein a) said valve axis and said sampling axis are disposed so that said valve body always prevents the gas sampling device from being inserted beyond said valve body into the vial;

b) said valve seat and said valve body are arranged so that the gas sampling device may be inserted far enough through said second seal so as to allow gas to be withdrawn from the interior of said tubular body member without displacing said valve body; and c) the gas sampling device makes a gas-tight seal to the second seal before the valve body is displaced; and wherein the exterior portion of said tubular body member is provided with a flange which overlaps the tap of a sample vial when said tubular body member is located in the mouth of that vial, said first seal comprising one of a rubber or plastic washer disposed between the top of the vial and said flange, and wherein said tubular body member is securable to the vial by a threaded retaining ring passed over said tubular body member and engaged with threads on the exterior of the vial.

* * * * *